(12) United States Patent
Huang et al.

(10) Patent No.: US 7,340,958 B2
(45) Date of Patent: Mar. 11, 2008

(54) METHODS FOR DETERMINING POTENTIAL CHARACTERISTICS OF A SPECIMEN BASED ON STRESS WAVE VELOCITY MEASUREMENTS

(75) Inventors: Chih-Lin Huang, Bellevue, WA (US); Clements C. Lambeth, Hot Springs, AR (US)

(73) Assignee: Weyerhaeuser Company, Federal Way, WA (US)

( * ) Notice: Subject to any disclaimer, the term of this patent is extended or adjusted under 35 U.S.C. 154(b) by 150 days.

(21) Appl. No.: 11/169,560

(22) Filed: Jun. 28, 2005

(65) Prior Publication Data

US 2006/0288784 A1    Dec. 28, 2006

(51) Int. Cl.
*G01N 29/04* (2006.01)
*G01N 29/18* (2006.01)
(52) U.S. Cl. .......................... 73/597; 73/644
(58) Field of Classification Search ................ 73/597, 73/598, 602, 632, 644, 579
See application file for complete search history.

(56) References Cited

U.S. PATENT DOCUMENTS

| | | | | |
|---|---|---|---|---|
| 4,838,085 A | * | 6/1989 | Pellerin et al. ............... | 73/597 |
| 4,845,989 A | * | 7/1989 | Titlow et al. .................. | 73/597 |
| 5,237,870 A | * | 8/1993 | Fry et al. ...................... | 73/588 |
| 6,598,477 B2 | * | 7/2003 | Floyd ........................... | 73/597 |
| 6,769,306 B2 | * | 8/2004 | Andrews et al. .............. | 73/597 |
| 6,871,545 B2 | * | 3/2005 | Huang ........................... | 73/597 |
| 7,043,990 B2 | * | 5/2006 | Wang et al. ................... | 73/597 |
| 7,066,007 B2 | * | 6/2006 | Ziegler et al. ............. | 73/12.12 |

OTHER PUBLICATIONS

Cilas C, "Variability in the rigidity of Coffea canephora Pierre stems determined by acoustic and analysis," Trees 16:23-27 (2002).
Almeras T, "Bending of apricot tree branches under the weight of axillary growth: test of a mechanical model with experimental data," Trees 16:5-15 (2002).

\* cited by examiner

*Primary Examiner*—Helen Kwok

(57) ABSTRACT

Methods are provided for using stress wave velocity measurements taken of a specimen at an early age to determine potential characteristics at a later age. The data may be used to, for example, evaluate specimens and/or families and/or clones at early ages to cut costs and/or to increase a rate of genetic gains. The specimens may be, for example, seedlings and/or explants of forestry and/or agricultural and/or horticultural species. The stress wave measurements may be obtained using conventional devices and/or systems and/or methods.

20 Claims, 5 Drawing Sheets

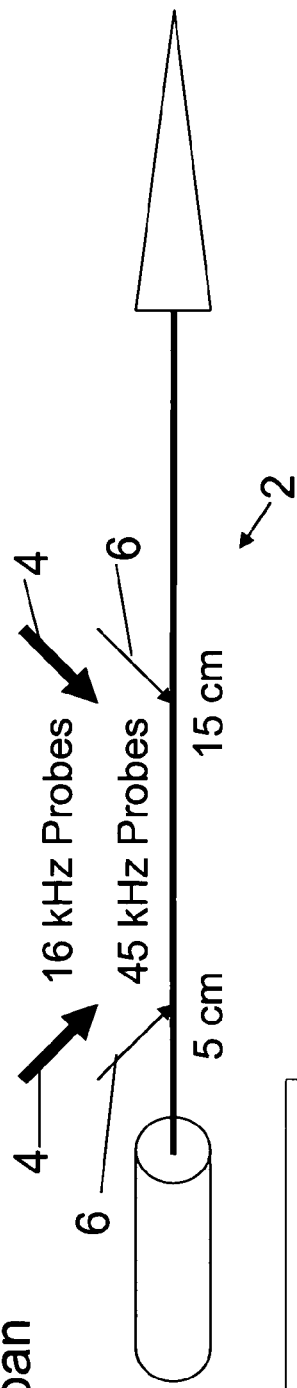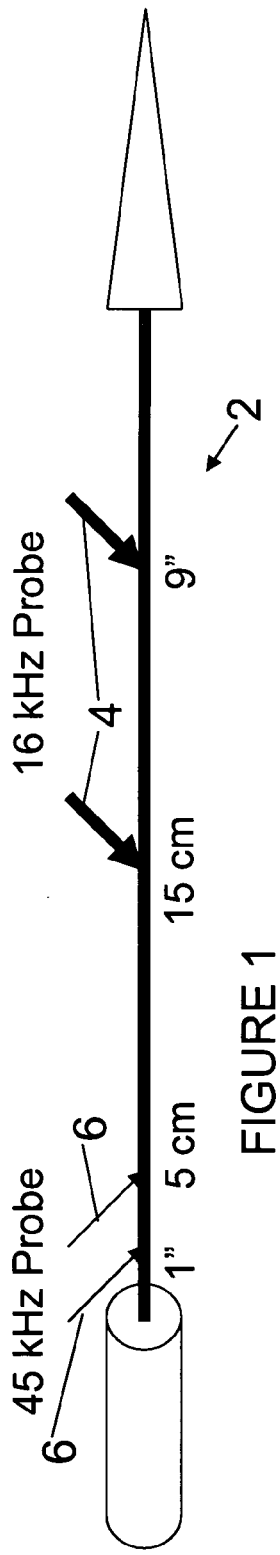
FIGURE 1

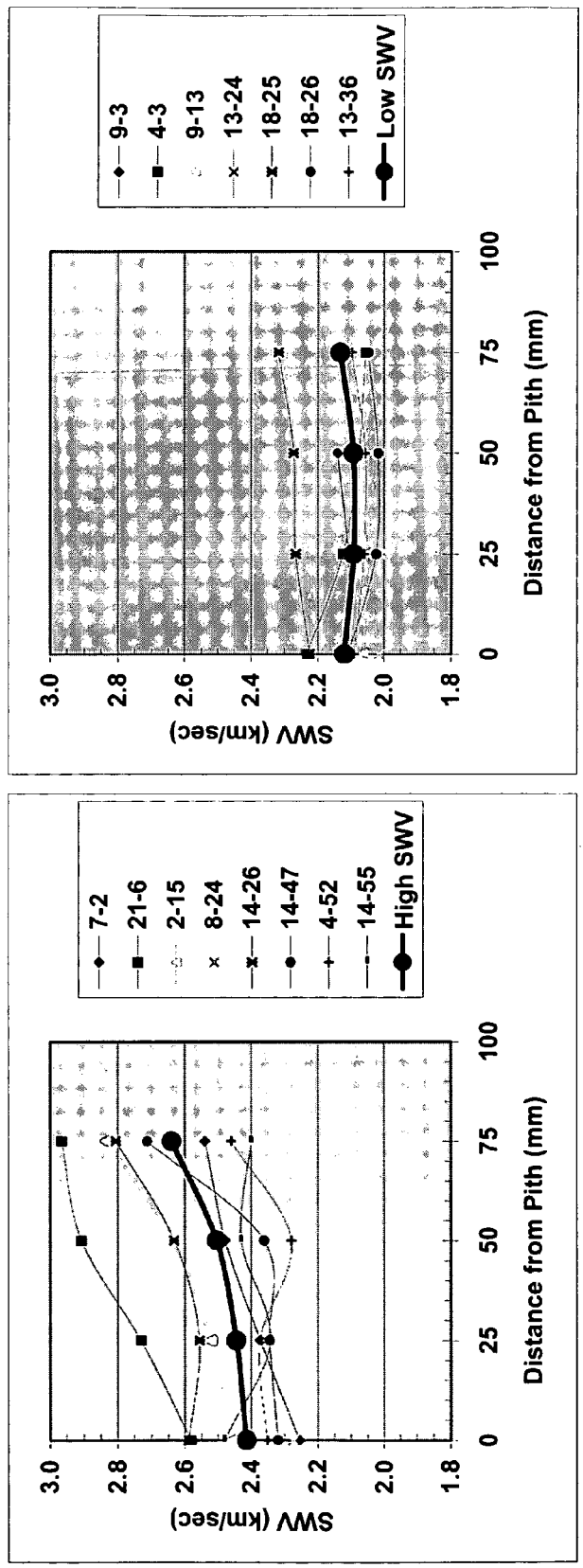
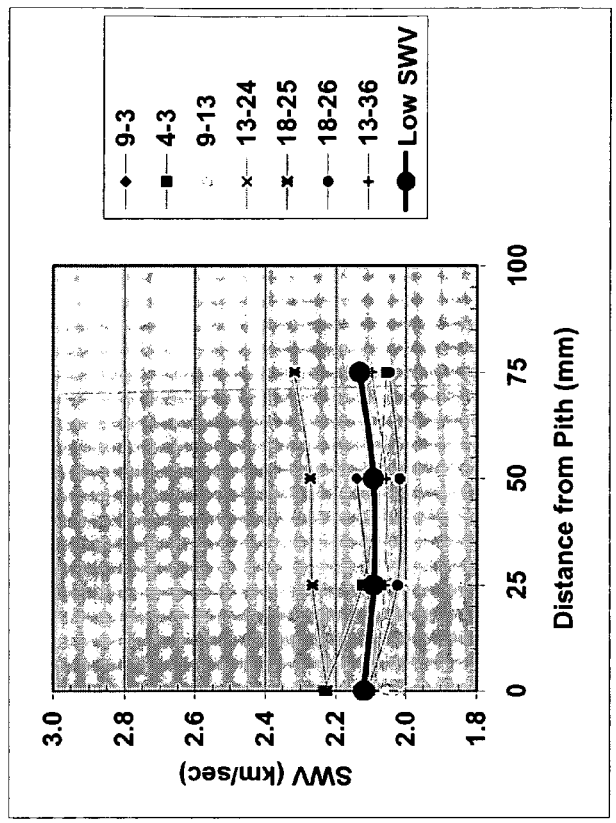
FIGURE 4B
FIGURE 4A

| Family Code | Stiffness Category | Seedling Sample Number | SWV At Age 6 Years In The Field (% of unimproved check) | 6-Month Stress Wave (meter/second) | 9-Month Stress Wave (meter/second) | (rank change) and Rate of Stress Wave Change % (9mo - 6mo)/6mo |
|---|---|---|---|---|---|---|
| L1 | Low | 74 | (8) -0.7 | (5) 885 | (11) 1389 | (-6) 36.9 |
| L2 | Low | 75 | (9) -2.1 | (12) 826 | (12) 1333 | (0) 37.5 |
| L3 | Low | 73 | (7) -0.3 | (3) 893 | (5) 1448 | (-2) 38.2 |
| L4 | Low | 75 | (11) -4 | (9) 870 | (8) 1429 | (+1) 39.4 |
| L5 | Low | 72 | (10) -3.2 | (8) 871 | (10) 1408 | (-2) 38.4 |
| L6 | Low | 75 | (12) -8.1 | (4) 885 | (4) 1449 | (0) 38.6 |
| H1 | High | 75 | (5) 6.7 | (6) 877 | (9) 1428 | (+3) 37.9 |
| H2 | High | 72 | (2) 9.8 | (2) 893 | (3) 1470 | (-1) 39.3 |
| H3 | High | 63 | (1) 12.6 | (1) 926 | (1) 1515 | (0) 39.1 |
| H4 | High | 73 | (4) 6.8 | (7) 877 | (2) 1471 | (+5) 40.6 |
| H5 | High | 74 | (3) 8.7 | (10) 862 | (7) 1429 | (+3) 39.6 |
| H6 | High | 75 | (6) 5.8 | (11) 847 | (6) 1430 | (+5) 40.8 |

Number in parentheses is the rank or rank change among the 12 families.

FIGURE 5

METHODS FOR DETERMINING POTENTIAL CHARACTERISTICS OF A SPECIMEN BASED ON STRESS WAVE VELOCITY MEASUREMENTS

FIELD OF THE INVENTION

This invention relates generally to the use of time of flight of propagating acoustic waves within a specimen an early age to determine potential characteristics of the specimen at a later age.

BACKGROUND OF THE INVENTION

It is generally known that acoustic measurement can be used to determine properties of materials, such as wood. These properties may include, for example, stiffness, strength, elasticity and other characteristics. In some embodiments, in which properties of material are being ascertained, a stress wave is induced into the material/sample/specimen. Next, a measurement is taken with respect to the time in which the stress wave travels from a first end to a second end of the sample. From this time interval, a velocity of the stress wave can be determined via the equation:

$$v=d/t$$

Where "v" is velocity of the stress wave; "d" is the distance traveled by the stress wave; and "t" is the time period of travel. This method of determining velocity is commonly referred to as a "time-of-flight" method. The velocity can, for example, be correlated to a modulus of elasticity for the wood, which is an indicator of the stiffness of the specimen. In general, an optimum stiffness of the specimen is desired to maximize the quality of the material.

The same may apply to agricultural and horticultural specimens. For example, the greater the stiffness exhibited by the specimen, the more likely the specimen is to possess desirable characteristics such as enhanced crown structure, increased lodging resistance, and minimized loss during mechanical harvesting. It should be understood that the term "specimen" in this application is meant to refer to either an individual tree, agricultural or horticultural product, or may refer also to a portion of the tree/product which may be obtained via, for example, removal of a branch or root segment and/or other removal measures known by those skilled in the art. In producing wood, agricultural and/or horticultural products, it is beneficial to ascertain characteristics of the products/specimens, as these characteristics can provide an indication of the quality of the family or quality, if any, of cloned specimens. Typically, these characteristics are ascertained when the specimens reach a mature age.

Unfortunately, uncertainties exist in forest, agriculture, and horticulture operations resulting from, for example, natural occurrences, regulatory restrictions, and/or financial resource commitments which can be very difficult to control in long-term experiments. In some cases, after years of field tests, project or experiment results may become irrelevant. In other cases, once an improved practice has been selected, the market may change. It has been estimated that more than 50% of forest research is not completed due to one or more of the above-mentioned factors. These difficulties may be reduced if information regarding specimens can be derived at an earlier stage of a project.

A need, therefore, exists for a method for using SWV measurements taken at an earlier age to determine potential characteristics of specimens and/or families and/or clones.

BRIEF DESCRIPTION OF THE DRAWINGS

The embodiments of the present invention are described in detail below with reference to the following drawings FIG. 1 is a front plan view of methods for obtaining stress wave velocity measurements in embodiments of the present invention;

FIGS. 4A and 4B are charts of stress wave velocity results for cloned specimens in an embodiment of the present invention; and FIG. 5 is a table displaying the results of stress wave measurements of seedlings at six months and at nine months in an embodiment of the present invention.

DETAILED DESCRIPTION OF THE INVENTION

Figure 2:
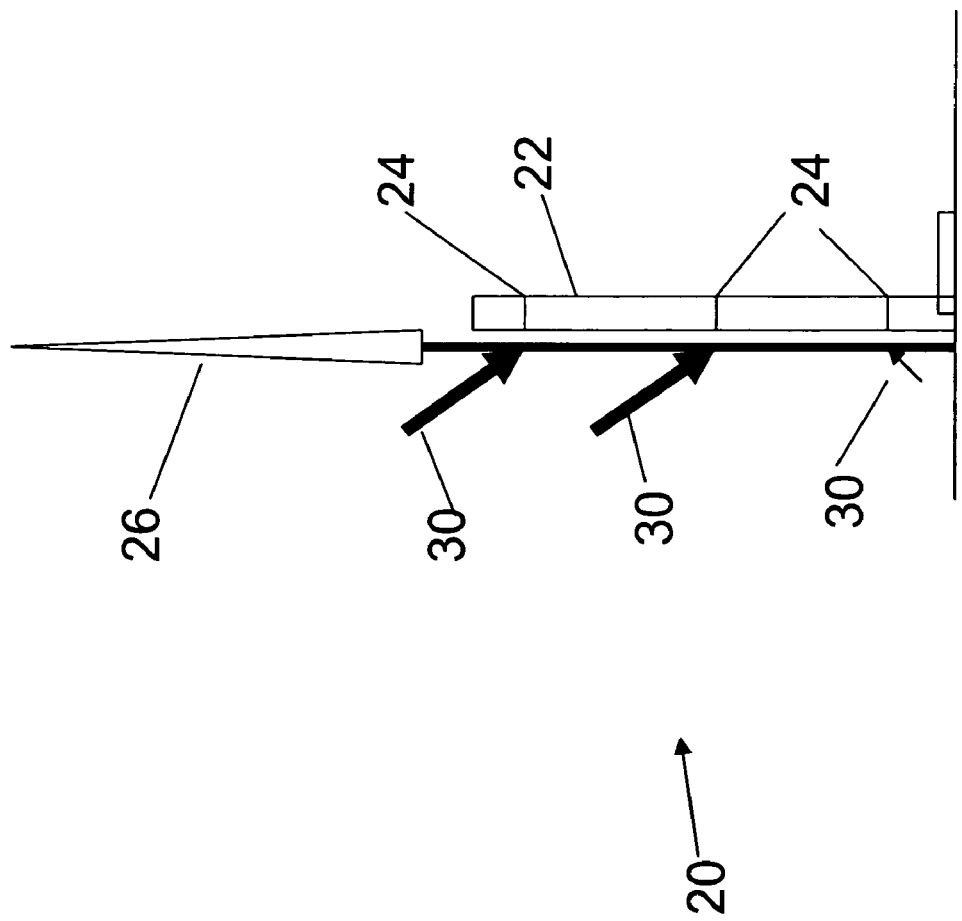
FIG. 2 is a plan view of a system for testing a specimen in an embodiment of the present invention.

The present invention relates to methods for using stress wave velocity measurements taken of a specimen at an early age to determine potential characteristics at a later age. The data may be used to, for example, evaluate specimens and/or families and/or clones and/or varieties at early ages to cut costs and/or to increase a rate of genetic gains. The specimens may be, for example, saplings, seedlings, and cloned materials and/or agricultural and/or horticultural species, such as, for example, cereal crops, coffee and orange crops. In terms of horticulture, the data may provide information regarding, for example, a crown structure of a tree. The stress wave measurements may be obtained using conventional devices and/or systems and/or methods.

Different apparatuses and/or systems, known by those skilled in the art, may be used to obtain the time of flight within a specimen. For example, single and/or multiple probe systems may be utilized. These apparatuses and/or systems may calculate velocity using those equations previously described. In an embodiment, an apparatus and/or system may contact the specimen and may induce a stress wave which may propagate through the specimen. Other known methods of stress wave inducement are also contemplated. The stress wave may travel from, for example, a first end of the specimen to a second end. The apparatus and/or system may then measure a pulse created at the first end and/or the second end.

In a single probe system, a probe, or transducer, is used to detect and record the waves which may reverberate back and forth within a specimen, such as an explant. Vegetative propagules may be provided via, for example, grafting, air layering, rooted cutting, tissue cultures, organogenesis, embryogenesis, vegetative propagation, or other methods known to those skilled in the art. The reverberation of waves back and forth within a specimen may be characterized as "multiple passes" through the specimen. In a two probe system, a first probe is placed at a first end of a specimen and a second probe is placed at a second end of the specimen. The first probe senses the initial pulse created by contact with the specimen. The second probe senses the pulse at the second end. This is commonly referred to as a "pitch-and-catch", or single pass, measurement. For standing saplings and seedlings, the pitch-and-catch method is more common due to the lack of a well-defined boundary of a standing sapling and/or seedling. It should be understood that the term "seedling" may reference any product formed from a seed or vegetative propagation. In other embodiments, stress waves may be induced through non-contact systems, such as, for example, ultrasound emitting devices or the like. The stress wave may be sensed by a single or multiple probe system.

The stress wave measurements may be taken a single time or at multiple times. More specifically, the measurements may be taken at an initial time $t_1$, and a subsequent time $t_2$. In an embodiment, a period of time is allotted between the time $t_1$, and the time $t_2$ to enable growth of the specimen. For example, in seedlings, a first measurement, at a time $t_1$, may be taken at six months. A second measurement, at a time $t_2$, may be taken at nine months. A change in stiffness between the time $t_1$ and the time $t_2$ may provide an indication of the potential of the specimen to provide desirable characteristics when the specimen matures. In an embodiment, a specimen may be tested more than twice. Moreover, the testing may be conducted in, for example, weekly increments for any amount of trials. Accordingly, it should be understood that any number of trials may be conducted, and further, any time increment may be utilized between the measurements to ascertain characteristics of a specimen. In another embodiment, the specimen may be tested once. The time range during which the testing may occur may be, for example, zero to five years.

Referring now to the drawings, FIG. 1 illustrates a specimen 2 which is measured at six months and at nine months of growth. The specimen may be a seedling and/or explant of a forest product, an agricultural product, or horticultural product. In an embodiment, one or more types of probes may be used to obtain SWV measurements at a first time $t_1$, such as six months of growth. It should be understood that the time $t_1$ may be any time suitable for testing the specimen at an early age. In an embodiment, a time range for testing at $t_1$ may be zero to five years. A first set of probes 4 may obtain measurements at a sampling frequency of 16 kHz. A second set of probes 6 may obtain measurements at a sampling frequency of 45 kHz. The frequency and the types of sensor may be dependent upon the size of the sample and the acoustic responses of the materials. The probes 4, 6 may be applied on the specimen 2, separated by a distance, such as, for example, 10 cm. It should be noted that, in various embodiments, the probes 4, 6 may be placed on the specimen 2 in any order and/or distance, i.e., with probes 4 being used first, followed by use of probes 6, or vice versa. In an embodiment, the probes 4, 6 may be used simultaneously. It should also be noted that the use of two or more probes may enable greater accuracy in stress wave velocity calculation via, for example, data averaging and other mathematical calculations.

The specimen 2 may also be measured at a time $t_2$, such as, for example, nine months of growth. In an embodiment, the time range for the time $t_2$ may be in a range from zero to five years after the time $t_1$. To this end, in an embodiment, the probes 4, 6 may be interchanged wherein a probe 4 may measure a signal of a propagating wave at a first end and a probe 6 may measure a signal of the propagating wave at an opposite end of the specimen 2. The probes 4, 6 may be separated by a distance of 10 cm in a first set and/or eight inches in a second set. It should be understood that the distances mentioned herein are solely for the purposes of example and should not be construed to limit any distances at which one of ordinary skill may set the probes apart. In this embodiment, use of differing probe types may allow the optimum results for testing delicate materials, small samples, and operating in a confined space such as near the ground of a planted seedling.

FIG. 2 illustrates a system 20 for measuring stress wave velocity within a specimen. The system 20 may have a stand 22 against which a specimen 26 may be placed. The stand 22 may have distance markers 24 which may provide a user with an indication as to placement of sensors, probes and/or other measuring devices for measuring stress wave velocity. Arrows 30 provide an indication of points on the specimen at which initial sensing of a stress wave and final sensing can be performed. This type of system 20 may be used for measuring in-ground and/or delicate specimens or similar types of specimens without causing, for example, any serious damage to an interior portion of the specimen as a result of standing alone while being tested.

Figure 3:
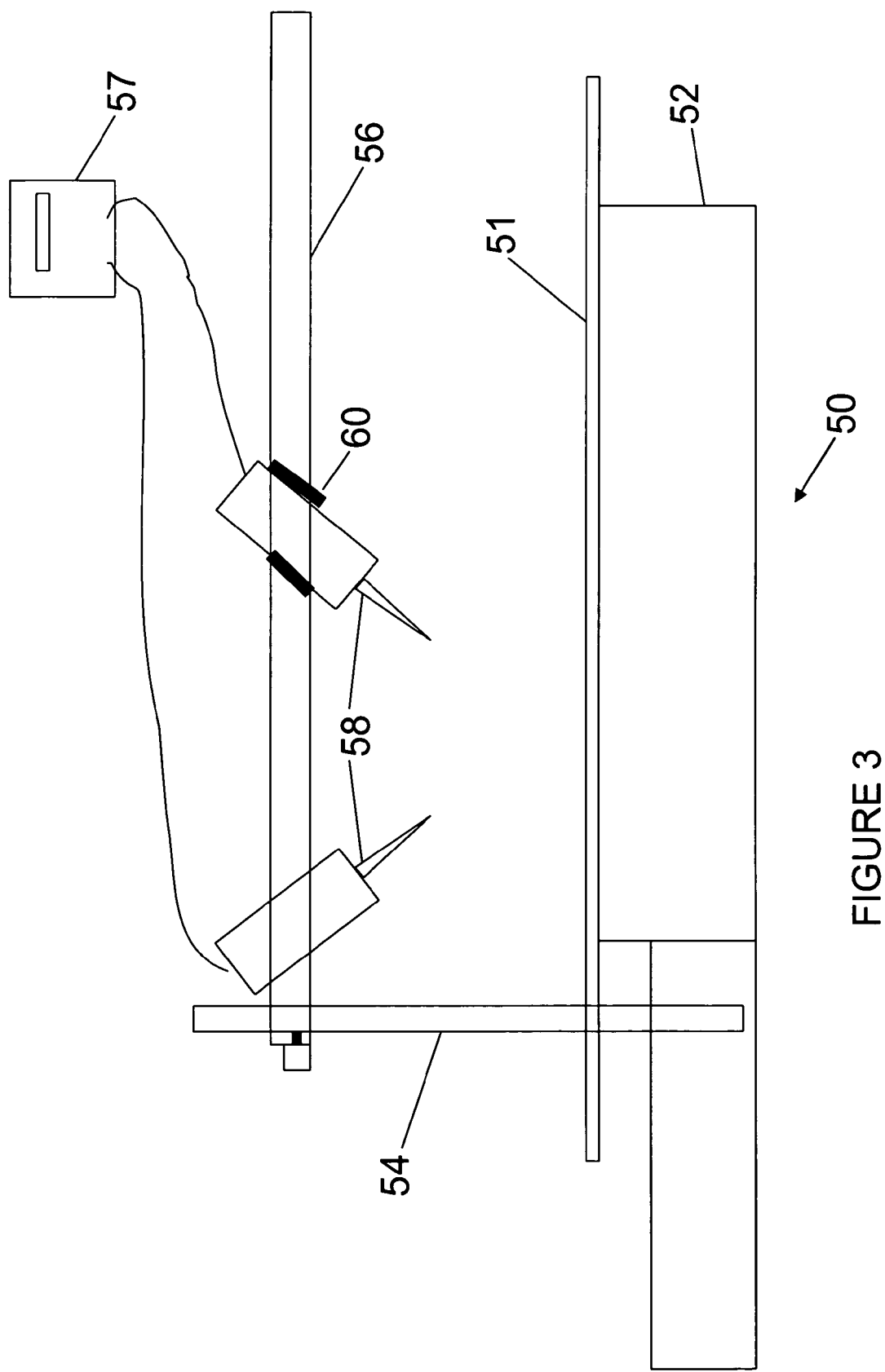
FIG. 3 is a plan view of another system for testing a specimen in an embodiment of the present invention.

FIG. 3 illustrates another system 50 for measuring stress wave velocity within a specimen. In this system 50, the specimen (not shown) may be placed across a platform 51 which may be adjacent to a backing or support layer 52. In the FIG., the platform 51 appears oriented in a horizontal manner. However, it should be noted that the platform 51 may be oriented in any position suitable for specimen placement and/or measurement. A stand 54 may be adjacent to the platform 51. A second platform 56 may extend from the stand 54. Probes or sensors 58 may be attached to the platform 56. A timer and/or CPU mechanism 57 may be in communication with the sensors 58 to enable measurement of stress wave velocity. These sensors 58 may be adjustable along a length of the platform 56. Any mechanism 60 known by those skilled in the art may be utilized to attach the sensors 58 and/or enable sliding or other adjustment along the length of the platform 56, such as removable clamps, other fastening devices, or the like. Adjustment of a distance between the sensors 58 may enable a range of distances at which the specimen be measured in terms of stress wave velocity. This type of system 50 may be used with, for example, delicate specimens to avoid damage to the specimens while testing. It may also ensure adequate coupling.

After obtaining the stress wave velocities of the propagating waves at six months and at nine months, a comparison may be made between the values. A difference between these values may provide an indication as to various characteristics of the specimen at a later age including, for example, stiffness, strength, or other features. More specifically, the initial value and/or a percentage change (the rate of stiffening and/or lignification), in the calculated velocity may provide an indication of a quality of the specimen. The percentage change may also provide an indication of the potential of the specimen to achieve desirable characteristics in later stages. In an embodiment, those specimens which demonstrate desired characteristics may be selected for future growth while less desirable specimens may be discarded. In this manner, a greater percentage of products (i.e., trees, agricultural products, horticultural products) grown by an individual/entity may demonstrate desired characteristics. Moreover, utilizing only desired specimens may raise the average level for the desired characteristic, in comparison to a product supply which included lesser quality specimens.

FIG. 5 illustrates a table of data taken of high and low ranked stiffness families of seedlings at six months and at nine months. A comparison is made between stress wave velocity measurements at six months and nine months in the form of a percentage change. The percentage change for each family can be ranked. Moreover, the families may be ranked at both the six month stage and the nine month stage, with a comparison between any changes in ranking for a family. For example, a family may have an average first stress wave velocity at six months that ranks second within the families also being tested at six months. This ranking may be compared with a second ranking at nine months based on the average stress wave velocities measured at that time for each of the families. In an embodiment, a rate of change can also be evaluated and used in combination with the absolute value of the stress wave velocity. For example, a user may evaluate whether the specimen demonstrates a stress wave value which is above what a standard value should be for the specimen. From these rankings/data, a family of seedlings may be selected based on desired quality level and/or other characteristics. For example, the family may be selected for desired mechanical properties at later ages. It should be noted that this method may be utilized for ranking seedlings within a family as well based on quality level and/or other characteristics. It should further be noted that this method may be used for agricultural products, horticultural products, cloned species, and/or other types of products including, but not limited to, cereal crops, coffee, orange crops and/or evaluating crown structure in trees.

Moreover, FIGS. 4A and 4B illustrate the use of the present invention to ascertain stress wave measurements at early ages of cloned specimens. FIG. 4A shows the results of testing high stiffness cloned specimens. FIG. 4B shows the results of testing low stiffness cloned specimens. From FIG. 4A it can be seen that high stiffness cloned specimens may demonstrate their stiffness at an early age and may increase in stiffness at a rate which is greater than a rate of increase for low stiffness cloned specimens. On the contrary, low stiffness cloned specimens display lower stiffness at an early age and may increase in stiffness at a lower rate than high stiffness specimens. This information may be useful when selecting a species to clone for future experimentation and/or commercial or other type of projects.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for using stress wave velocity measurements to evaluate a specimen at an early age, the method comprising the steps of:
    inducing a first stress wave into the specimen at a time $t_1$;
    measuring a first stress wave velocity at the time $t_1$ based on travel of the first stress wave through the specimen;
    inducing a second stress wave into the specimen at a time $t_2$;
    measuring a second stress wave velocity at the time $t_2$ based on travel of the second stress wave through the specimen;
    measuring a difference between the first stress wave velocity and the second stress wave velocity; and
    correlating the difference to a quality level for the specimen at a time subsequent to the time $t_2$.

2. The method of claim 1 further comprising the step of:
    inducing a stress wave into the specimen at a time $t_3$ subsequent to the time $t_2$.

3. The method of claim 2 further comprising the step of:
    measuring a third stress wave velocity at the time $t_3$ based on travel of the third stress wave through the specimen.

4. The method of claim 1 wherein the specimen is within a variety of specimens.

5. The method of claim 1 wherein the specimen is a cloned product.

6. The method of claim 1 wherein the specimen is an agricultural product.

7. The method of claim 1 wherein the specimen is a horticultural product.

8. A method for using stress wave velocity measurements at an early age to evaluate a group of specimens within a plurality of groups of specimens, the method comprising the steps of:
    inducing a first stress wave into each of the specimens of each group at a time $t_1$;
    measuring a first stress wave velocity at the time $t_1$ for each of the specimens based on travel of the first stress wave through each of the specimens;
    averaging a first stress wave velocity for each group based on the stress wave velocities calculated for each specimen within the group at the time $t_1$;
    inducing a second stress wave into each of the specimens of each group at a time $t_2$;
    measuring a second stress wave velocity for each of the specimens at the time $t_2$ based on travel of the second stress wave through each of the specimens;
    averaging a second stress wave velocity for each group based on the stress wave velocities calculated for each specimen within the group at the time $t_2$;
    calculating a difference between the averaged first stress wave velocity and the averaged second stress wave velocity for each group;
    comparing the differences associated with each of the groups;
    correlating at least one of the differences for one of the groups to a quality level for that group.

9. The method of claim 8 wherein the plurality of specimens comprise one or more families of specimens.

10. The method of claim 8 wherein the plurality of specimens comprise one or more cloned varieties of specimens.

11. The method of claim 8 wherein the plurality of specimens comprise one or more agricultural varieties.

12. The method of claim 8 wherein the plurality of specimens comprise one or more horticultural varieties.

13. The method of claim 8 further comprising the step of:
    selecting at least one of the groups for continued growth based on the quality level.

14. The method of claim 8 wherein the stress waves are measured by one or more probes.

15. The method of claim 8 wherein the stress waves are measured at one or more sampling frequencies.

16. The method of claim 8 further comprising the step of:
    measuring a third stress wave velocity for one or more specimens at a time $t_3$.

17. The method of claim 8 wherein at least one of the specimens for which stress wave velocity is measured is growing as the measurement is being taken.

18. The method of claim 8 wherein the time $t_1$ occurs within a time range of zero to five years.

19. The method of claim 8 wherein the time $t_2$ occurs within a time range from zero to three years after the time $t_1$.

20. The method of claim 8 comprising the step of:
    ranking one or more groups based on the quality level for the group.

* * * * *